US00PP35460P2

(12) United States Plant Patent
Kleinwee

(10) Patent No.: US PP35,460 P2
(45) Date of Patent: Nov. 7, 2023

(54) ***PETUNIA* PLANT NAMED 'PEHY0078'**

(50) Latin Name: *Petunia hybrida*
Varietal Denomination: PEHY0078

(71) Applicant: SYNGENTA CROP PROTECTION AG, Basel (CH)

(72) Inventor: Theodorus Cornelis Maria Van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/976,948

(22) Filed: Oct. 31, 2022

(51) Int. Cl.
*A01H 5/02* (2018.01)
*A01H 6/82* (2018.01)

(52) U.S. Cl.
USPC ..... Plt./356.15

(58) Field of Classification Search
USPC ..... Plt./356.1, 356.15
See application file for complete search history.

*Primary Examiner* — Susan McCormick Ewoldt
(74) *Attorney, Agent, or Firm* — Dale Skalla

(57) ABSTRACT

A new *Petunia* plant named 'PEHY0078' particularly distinguished by its small flowers, a white flower color, medium early flowering and a semi trailing plant habit.

1 Drawing Sheet

Latin name of the genus and species of the plant claimed: *Petunia hybrida.*

Varietal denomination: 'PEHY0078'.

BACKGROUND OF THE NEW PLANT

The present invention comprises a new *Petunia*, botanically known as *Petunia hybrida*, and hereinafter referred to by the variety name 'PEHY0078'.

'PEHY0078' is a product of a planned breeding program. The new cultivar has small flowers, a white flower color, medium early flowering and a semi trailing plant habit.

'PEHY0078' originated from a hybridization made in June 2017 in a controlled breeding environment in Enkhuizen, The Netherlands. The female parent was the proprietary selection 'BB2080-1V'. Compared to 'PEHY0078', it is more vigorous, has a much stronger vein in the flower, is earlier flowering and has a lavender flower color.

The male parent of 'PEHY0078' was the variety 'Dekko deep lavender' (not patented); a plant with lavender flower color, less vigorous and with a bit more mounding plant habit.

The resulting seeds were sown in August 2017. 'PEHY0078' was selected as one flowering plant within the progeny of the stated cross in November 2017 in a controlled environment in Enkhuizen, The Netherlands.

The first act of asexual reproduction of 'PEHY0078' was accomplished when vegetative cuttings were propagated from the initial selection in January 2018 in a controlled environment in Enkhuizen, The Netherlands.

BRIEF SUMMARY OF INVENTION

Horticultural examination of plants grown from cuttings of the plant initiated in January 2018 and continuing thereafter, has demonstrated that the combination of characteristics as herein disclosed for 'PEHY0078' are firmly fixed and are retained through successive generations of asexual reproduction.

'PEHY0078' has not been observed under all possible environmental conditions. The phenotype may vary significantly with variations in environment such as temperature, light intensity, and day length.

A Plant Breeder's Right for this cultivar has been applied for in the European Union on Sep. 12, 2022, No. 2022/2062. 'PEHY0078' has not been made publicly available prior to the effective filing date of this application, notwithstanding any disclosure that may have been made less than one year prior to the effective filing date of this application by the inventor or another who obtained 'PEHY0078' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
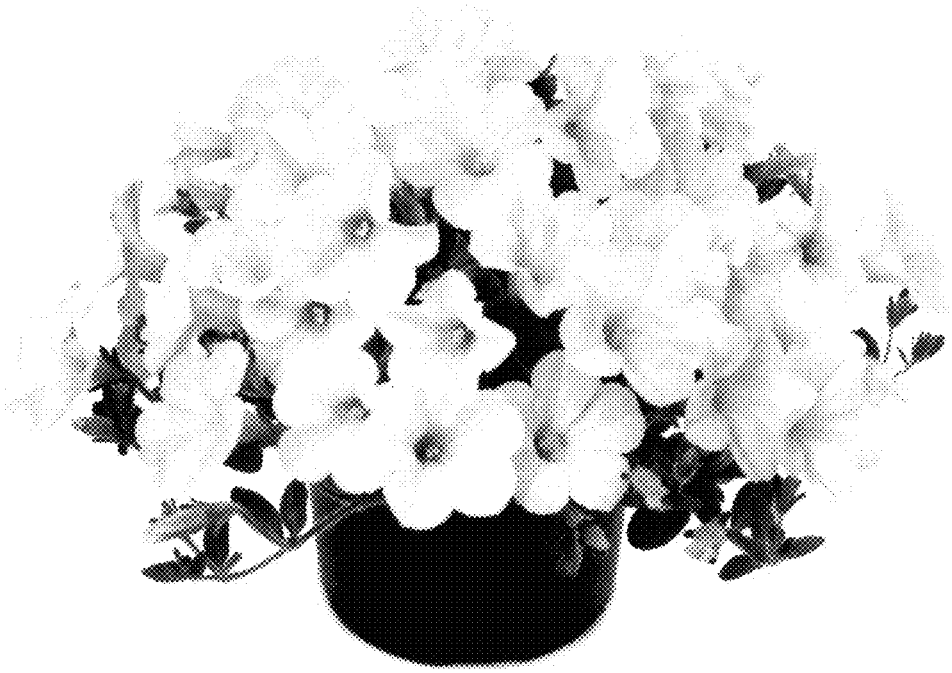
Figure 2:
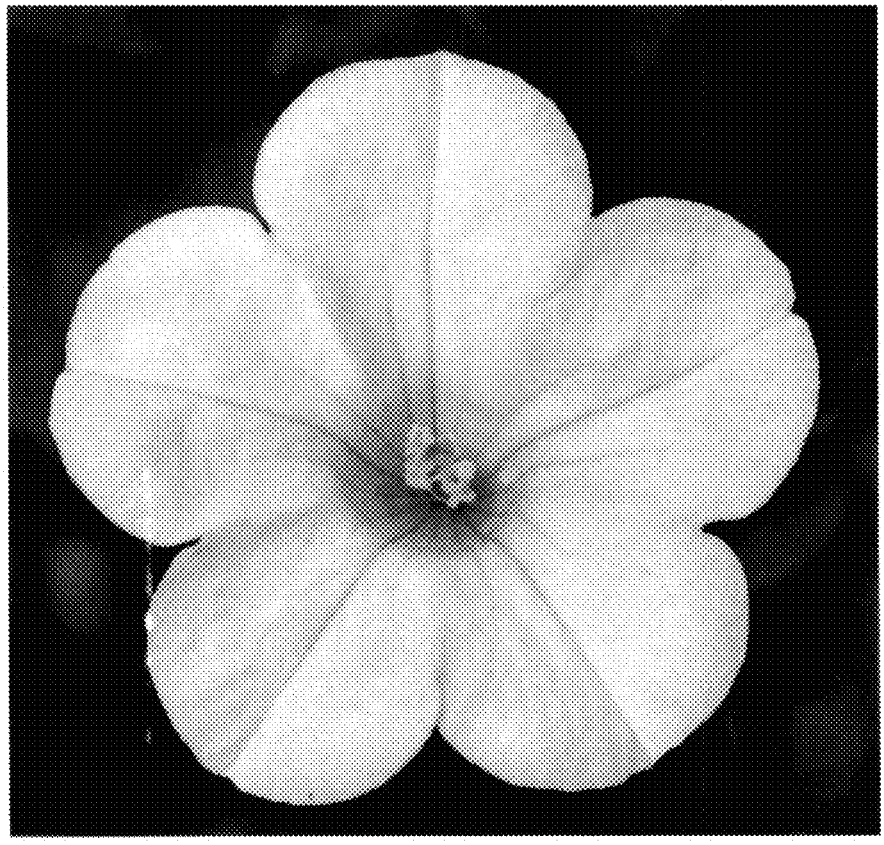

The accompanying photographic drawings show typical flower and foliage characteristics of 'PEHY0078' with colors being as true as possible with an illustration of this type. The photographic drawings show in FIG. 1 a flowering plant of the new variety and in FIG. 2 a close-up of the flower.

DETAILED BOTANICAL DESCRIPTION

The aforementioned photographs were taken in September 2021 from plants growing indoor in 12 cm pots in Andijk, The Netherlands. These plants were approximately 12 weeks of age.

The plant descriptions and measurements were taken in September 2022 in Andijk, The Netherlands on outdoor plants grown in 35 cm containers. These plants were about 16 weeks old.

Color references are made to The Royal Horticultural Society Colour Chart (R.H.S.) 2001.

TABLE 1

DIFFERENCES BETWEEN THE NEW VARIETY 'PEHY0078' AND A SIMILAR VARIETY

| | 'PEHY0078' | 'PEHY0040' (U.S. Plant Pat. No. 32,230) |
|---|---|---|
| Earliness: | Medium early | Late flowering |
| Flower shape: | Flat | Cup shaped |
| Floriferousness: | Rich flowering | Rather poor flowering |
| Foliage color: | Green | Greyish-green |

Plant:
- *Form, growth and habit.*—Mounding plant habit.
- *Plant height.*—19 cm.
- *Plant height (inflorescence included).*—22 cm.
- *Plant diameter (width).*—Approximately 40 cm.

Roots:
- *Number of days to initiate and produce roots.*—16 days at about 22° C.
- *Type.*—Fine, fibrous, free branching.
- *Color.*—RHS N158D.

Foliage:
- *Arrangement.*—Alternate, simple; sometimes opposite, decussate.
- *Immature leaf, color upper surface.*—RHS 137C.
- *Immature leaf, color lower surface.*—RHS 137D.
- *Mature leaf, color upper surface.*—RHS 137C.
- *Mature leaf, color lower surface.*—RHS 137D.
- *Length.*—3.5-4.5 cm.
- *Width.*—1.6 cm.
- *Shape.*—Ovate.
- *Base shape.*—Acuminate.
- *Apex shape.*—Acute.
- *Margin.*—Entire.
- *Texture, upper surface.*—Densely covered with short hair.
- *Lower surface.*—Densely covered with short hairs.
- *Color of veins, upper surface.*—RHS 144A.
- *Color of veins, lower surface.*—RHS 144A.
- *Petiole color.*—RHS 144A.
- *Length.*—0.2 cm.
- *Diameter.*—0.2 cm.
- *Petiole texture.*—Densely covered with short hairs.

Stem:
- *Quantity of main branches per plant.*—4-5.
- *Color of stem.*—RHS 144A.
- *Length of stem.*—19 cm.
- *Diameter.*—0.3 cm.
- *Length of internodes.*—1.5-2.5 cm.
- *Texture.*—Dense, mostly glandular short hairs.
- *Color of pedicel.*—RHS 144A.
- *Length of pedicel.*—2.5 cm.
- *Diameter of pedicel.*—0.2 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium early flowering in greenhouse, flowering throughout the summer months.
- *Quantity of inflorescences per plant.*—Approximately 70.
- *Lastingness of individual blooms on the plant.*—About 7 days.
- *Fragrance.*—Rather strong smell.

Bud (just when opening):
- *Color.*—RHS 157D at top, RHS N144B towards base.
- *Length.*—2.0 cm.
- *Width.*—0.4 cm.
- *Shape.*—Oblong.

Immature inflorescence:
- *Flower horizontal diameter.*—2.4 cm.
- *Color petals, upper surface.*—RHS 155A.
- *Color petals, lower surface.*—RHS 155A.

Mature flower:
- *Flower horizontal diameter.*—3.4 cm.
- *Flower height (vertical).*—3.0 cm.
- *Color upper surface.*—RHS 155A.
- *Color lower surface.*—RHS 155A.
- *Conspicuousness of veins.*—Weak to medium.
- *Apex shape.*—Mostly rounded but occasionally retuse or acuminate.
- *Margin.*—Entire.
- *Waviness of margin.*—Medium.
- *Petal lobation.*—Medium.
- *Petal texture, upper surface.*—Smooth.
- *Petal texture, lower surface.*—Smooth, occasionally a short hair mainly along veins.
- *Corolla tube color outside.*—RHS 154C with veins RHS 154A.
- *Corolla tube color inside.*—RHS 21B, deeper in tube RHS 151A.
- *Conspicuousness of veins in tube.*—Medium.
- *Corolla tube length.*—2.0 cm.
- *Corolla tube texture, outside.*—Dense and short glandular hairs.
- *Corolla tube texture, inside.*—Glabrous.

Calyx:
- *Color of sepal, upper surface.*—RHS 137C.
- *Color of sepal, lower surface.*—RHS 137D.
- *Length.*—1.0 cm.
- *Width.*—0.2 cm.
- *Shape.*—Ensiform.
- *Apex shape.*—Acute.
- *Base.*—Fused.
- *Margins.*—Entire.
- *Texture, upper surface.*—Densely covered with short glandular hairs.
- *Lower surface.*—Densely covered with short glandular hairs.

Reproductive organs:
- *Pistil.*—1.
- *Length.*—2.2 cm.
- *Style color.*—RHS 149C.
- *Style length.*—1.5 cm.
- *Stigma color.*—RHS 150B, RHS N144B in center of stigma.
- *Stamens.*—
- *Quantity per flower.*—5.
- *Color of filaments.*—RHS 157D.
- *Length filaments.*—1.7 cm.
- *Anther color.*—RHS 18D.
- *Anther length.*—0.2 cm.
- *Anther shape.*—Elliptical.
- *Color of pollen.*—RHS 13D.
- *Pollen amount.*—Abundant.
- *Fertility/seed set.*—Has not been observed on this hybrid.
- *Disease/pest resistance.*—Has not been observed on this hybrid.

What is claimed is:

1. A new and distinct variety of *Petunia* plant named 'PEHY0078' substantially as illustrated and described herein.

* * * * *